United States Patent [19]

Soderquist et al.

[11] Patent Number: 5,082,429
[45] Date of Patent: Jan. 21, 1992

[54] PERISTALTIC PUMP

[75] Inventors: Charles E. Soderquist, Barrington; Steven P. Hellstrom, Roselle, both of Ill.

[73] Assignee: Cole-Parmer Instrument Company, Chicago, Ill.

[21] Appl. No.: 573,904

[22] Filed: Aug. 28, 1990

[51] Int. Cl.⁵ .................. F04B 43/12; F04B 45/08
[52] U.S. Cl. .................. 417/477; 604/153; 128/DIG. 12
[58] Field of Search ............... 417/474, 475, 476, 477; 604/153; 128/DIG. 12

[56] References Cited

U.S. PATENT DOCUMENTS

| | | |
|---|---|---|
| 1,988,337 | 1/1935 | Santiago et al. |
| 2,804,023 | 8/1957 | Lee |
| 3,366,071 | 1/1968 | Dutler |
| 3,567,345 | 3/1971 | Ballentine ............... 417/477 |
| 3,723,030 | 3/1973 | Gelfand ............... 417/477 X |
| 3,762,836 | 10/1973 | De Vries ............... 417/238 |
| 3,791,777 | 2/1974 | Papoff et al. ............... 417/477 X |
| 3,927,955 | 12/1975 | Spinosa et al. ............... 417/477 |
| 4,025,241 | 5/1977 | Clemens ............... 417/477 |
| 4,043,712 | 8/1977 | Azzolini ............... 417/477 |
| 4,138,205 | 2/1979 | Wallach ............... 417/460 |
| 4,142,845 | 3/1979 | Lepp et al. ............... 417/477 |
| 4,155,362 | 5/1979 | Jess ............... 128/214 F |
| 4,187,057 | 2/1980 | Xanthopoulos ............... 417/477 X |
| 4,189,286 | 2/1980 | Murry et al. ............... 417/477 |
| 4,210,138 | 7/1980 | Jess et al. ............... 417/477 X |
| 4,211,519 | 7/1980 | Hogan ............... 417/477 |
| 4,217,993 | 8/1980 | Jess et al. ............... 222/14 |
| 4,231,725 | 11/1980 | Hogan ............... 417/477 |
| 4,288,205 | 9/1981 | Henk ............... 417/477 |
| 4,473,342 | 9/1984 | Iles ............... 417/360 |
| 4,519,754 | 5/1985 | Minick ............... 417/477 |
| 4,522,571 | 6/1985 | Little ............... 417/476 |
| 4,552,516 | 11/1985 | Stanley ............... 417/477 |
| 4,568,255 | 2/1986 | Lavender et al. ............... 417/477 |
| 4,673,334 | 6/1987 | Allington et al. ............... 417/53 |
| 4,735,558 | 4/1988 | Kienholz et al. ............... 417/477 |
| 4,813,855 | 3/1989 | Leveen et al. ............... 417/477 |
| 4,886,431 | 12/1989 | Soderquist et al. ............... 604/153 X |
| 4,925,376 | 5/1990 | Kahler ............... 417/477 |

FOREIGN PATENT DOCUMENTS

| | | |
|---|---|---|
| 100309 | 9/1973 | Fed. Rep. of Germany |
| WO82/04291 | 12/1982 | PCT Int'l Appl. |
| WO83/01984 | 6/1983 | PCT Int'l Appl. |
| 1383857 | 2/1975 | United Kingdom |
| 2076476A | 12/1981 | United Kingdom |
| 2094410A | 9/1982 | United Kingdom |
| 2109474A | 6/1983 | United Kingdom |

Primary Examiner—Richard A. Bertsch
Assistant Examiner—Michael I. Kocharov
Attorney, Agent, or Firm—Fitch, Even, Tabin & Flannery

[57] ABSTRACT

A peristaltic pump providing a mechanism for varying tubing occlusion in combination with a camming mechanism which facilitates opening and closing of the pump.

8 Claims, 2 Drawing Sheets

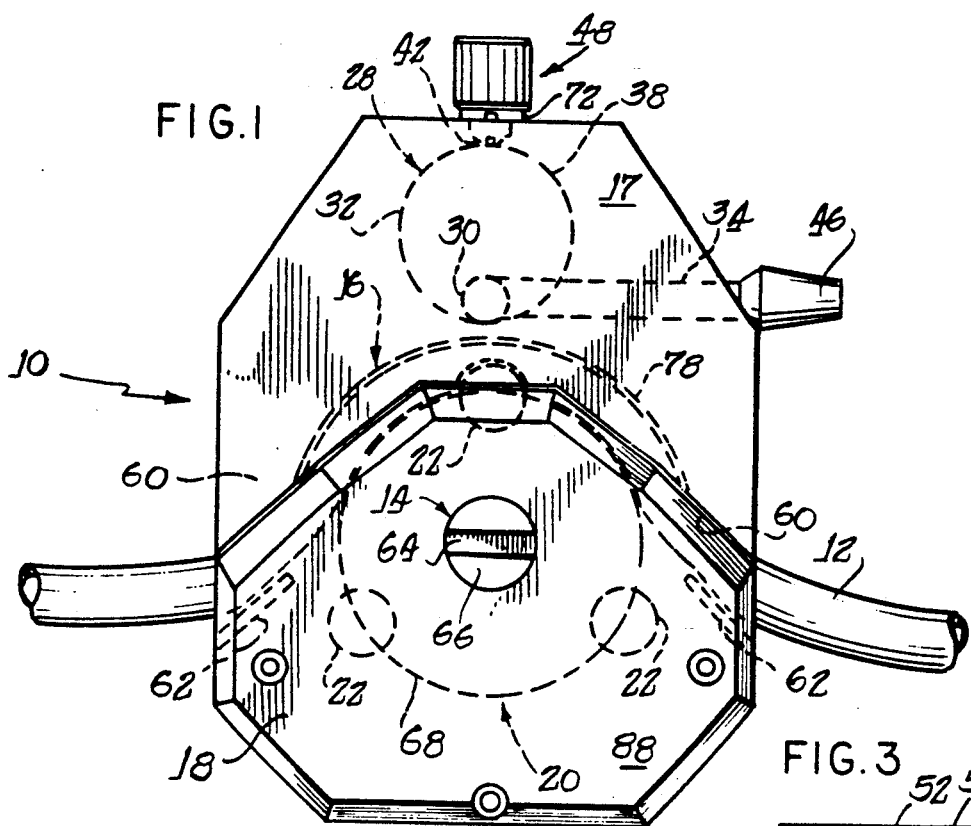
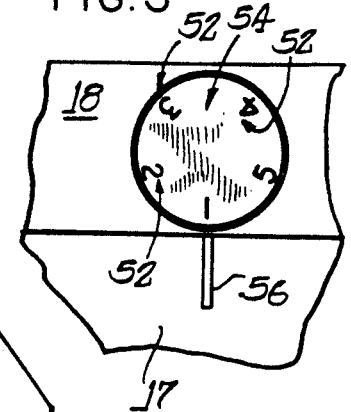
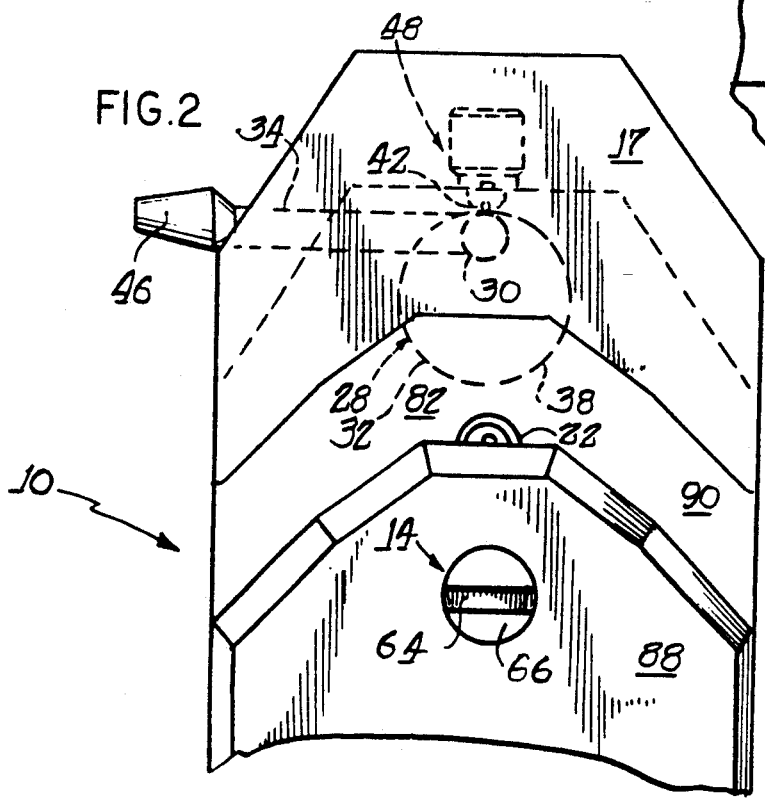

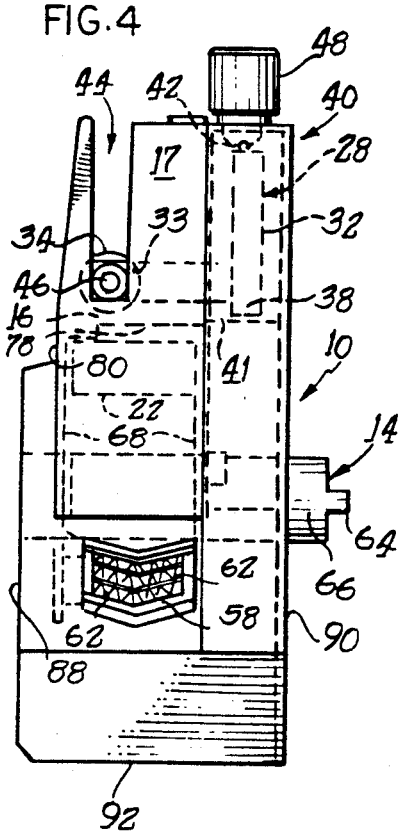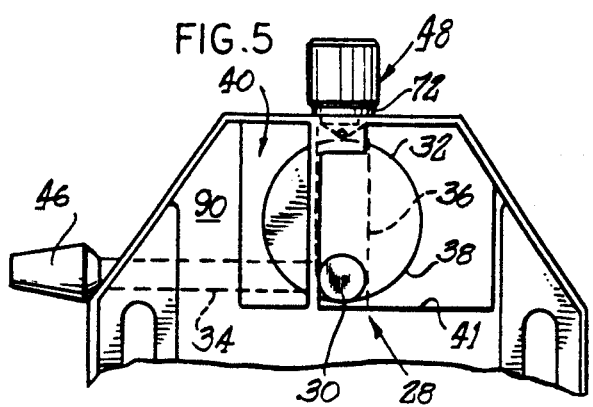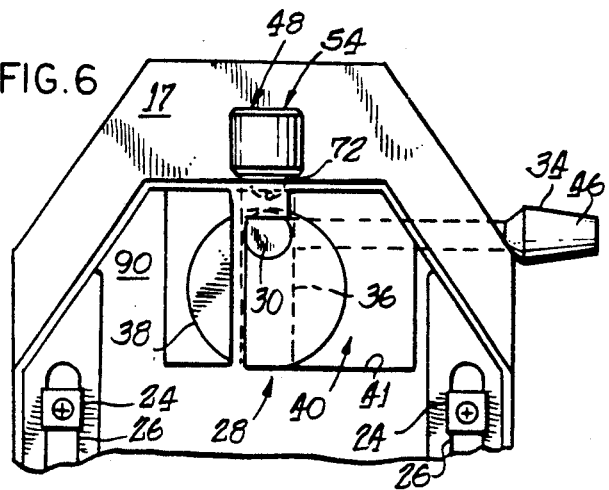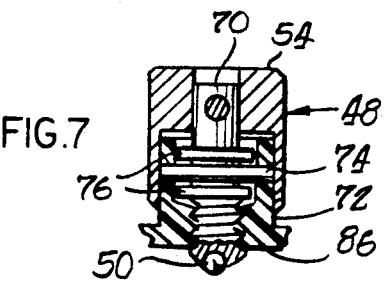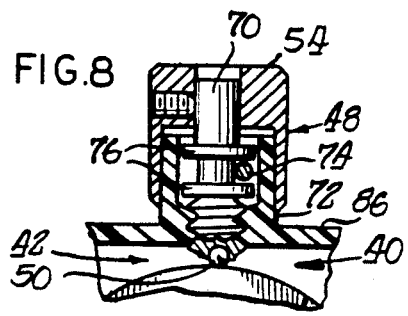

PERISTALTIC PUMP

BACKGROUND OF THE INVENTION

The invention relates generally to peristaltic pumps, and more particularly to a peristaltic pump having means to facilitate loading and unloading of tubing.

Peristaltic pumps are preferred for certain applications due to their ability to pump fluids through tubing without any contact between pump components and the fluid being pumped. In certain contexts, such as laboratory uses, it may be desirable to change tubing frequently in a particular pump. Various efforts have been made to enable removal and insertion of tubing with relatively little time and effort.

The provision of a mechanism for quickly and easily opening the pump to permit loading and unloading of tubing, and closing the pump to permit peristaltic pumping, involves several considerations. Among these is the fact that in the closed position, the occlusion bed must be stably supported in a desired spatial relationship to the rotor, notwithstanding relatively high dynamic pumping forces directed radially outward against the occlusion bed during pumping. The locking mechanism must be capable of withstanding such forces and operational loads without loosening. Any increase in the distance between the occlusion bed and the rotor changes occlusion and consequently results in variation of flow rates. Other considerations that must be taken into account are the need for the pump to be capable of economical manufacture, and durable so as to withstand normal operating loads without undue wear.

U.S. Pat. No. 4,813,855 discloses a mechanism which provides a practical and effective means to facilitate changing of tubing. The mechanism employs a cam arrangement whereby the pump is opened or closed by a single stroke of a manually-operable handle through an arc of about 180°.

The present invention relates to an improved mechanism which employs the advantages of the mechanism described in U.S. Pat. No. 4,813,855 and provides additional advantages as set forth below.

SUMMARY OF THE INVENTION

In accordance with the invention, there is provided a peristaltic pump having means to enable variable occlusion in combination with a quick-release mechanism in which the occlusion bed is displaced between an open and closed position by a single stroke of a handle associated with a camming mechanism.

In accordance with a feature of the invention, the means to enable variable occlusion employ direct contact between an adjustment screw assembly and a cam, such that rotation of the screw assembly varies the bearing surface against which the cam acts, thereby enabling the closed position of the occlusion bed to be determined with precision.

Variation of occlusion enables greater control over pump operation. Generally, increased pressure requires increased occlusion. However, increased occlusion generally decreases tube life. Thus, the provision of means for varying occlusion enables the pump to be operated with sufficient occlusion to accommodate pressure in each particular application, without unduly decreasing tube life by providing greater occlusion than necessary during low pressure usage.

In accordance with a further feature of the invention, the adjustment screw assembly is provided with visually discernible indicia to facilitate repeatability of occlusion adjustments, and is constrained to a limited range of rotation of about 360°.

Further features and advantages of the invention will become apparent form the text set forth below, and the accompanying drawings.

BRIEF DESCRIPTION OF THE DRAWINGS

FIG. 1 is a front elevational view of a pump in accordance with the invention, shown in closed position;

FIG. 2 is a fragmentary front elevational view similar to FIG. 1, but with the pump shown in open position;

FIG. 3 is a fragmentary plan view of the pump of FIG. 1, showing the adjustment screw assembly on an enlarged scale;

FIG. 4 is a side elevational view of the pump of FIG. 1;

FIG. 5 is a fragmentary rear elevational view of the pump of FIG. 1, showing the pump in closed position;

FIG. 6 is a fragmentary rear elevational view similar to FIG. 5, but showing the pump in open position;

FIG. 7 is a sectional elevational view of the adjustment screw assembly of the pump of FIG. 1, shown in a first orientation; and FIG. 8 is a sectional elevational view of the adjustment screw assembly of FIG. 7, shown in an orientation displaced 90° from that of FIG. 7.

DETAILED DESCRIPTION OF PREFERRED EMBODIMENT

The invention is preferably embodied in a peristaltic pump 10 in which a length of tubing 12 is secured between a rotor 14 and an occlusion bed 16 on a pump head 17 such that rotation of the rotor effects displacement of fluid along the length of the tubing. The rotor 14 and head 17 are supported on base 18 which comprises upstanding front and back walls 88 and 90 respectively, and a bottom wall 92 connecting the front and back walls.

The rotor 14 is supported for rotation between the front and back walls of the base 18, and comprises a drive shaft 66 and support structure 20 with a plurality of rollers 22 mounted thereon. The support structure includes a pair of spaced annular supports 68 fixed to the drive shaft. As is conventional, each of the rollers 22 extends between the annular supports 68 and has internal bearings so as to be rotatable about its axis, which is parallel to that of the rotor 14. An integral drive shaft coupling 64 at one end enables connection to commercially available pump drive means.

The occlusion bed 16 provides a pressure surface 78 shaped as a portion of a circular cylinder, parallel to the axis of the rotor 14. Undesired displacement of the tubing in the direction of the axis of the rotor is precluded by a lip or rim 80 extending downwardly along the forward edge of the pressure surface, and by the forward surface 82 of the back wall of the base. When the pump is in the closed position, the pressure surface 78 is approximately at a uniform radius from the axis of the pump rotor, thereby providing for substantially uniform occlusion over the entire pressure surface.

The pump head 17 is movable radially relative to the rotor 14, between an open position (see FIGS. 2 and 6) in which the occlusion bed is spaced from the rotor by a sufficient distance to permit loading and unloading of the tubing, and a closed position (see FIGS. 1, 4 and 5) in which the occlusion bed 16 is in close proximity to the rotor 14 to enable the tubing 12 to be compressed by the rollers 22 as the rotor rotates.

The pump head 17 is supported on the back wall 90 of the base and is constrained for rectilinear travel by a pair of slide members 24 (FIG. 6) extending through vertical slots 26 in the back wall 90, and by a pair of vertical ribs on the head 17 which slide in corresponding complementary grooves on the base 18. Upward and downward travel of the head 17 relative to the base 18 is effected by pivoting of a camshaft assembly 28. The camshaft assembly comprises a camshaft 30 which extends through a closely fitting bore in the pump head 17 and a vertical slot 36 in the base 18, a cam 32 fixed to the camshaft 30, and an arm or handle 34 extending radially outward from the camshaft to enable it to be pivoted manually through an arc of about 180°. The handle 34 is in large part disposed within a deep channel 44 in the pump head, with the outer end 46 protruding therefrom.

The base 18 has means for engaging the cam 32 such that the cam 32 has a limited range of vertical motion relative to the base. The cam is preferably a circular disk having a circular cylindrical peripheral surface 38, and is disposed eccentrically on the camshaft 30 so that rotation of the camshaft 30 effects upward or downward displacement of the camshaft 30 in the slot 36 and corresponding upward or downward displacement of the pump head 17 relative to the base 18.

In the illustrated embodiment, the cam 32 is disposed in a recess 40 at the upper end of the rear wall 90 of the base 18. As viewed in FIGS. 5 and 6, the recess 40 is dimensioned with sufficient width to accommodate sideways displacement of the cam 32 to the right of the camshaft 30. A vertical strut 84 extends from the bottom to the top of the recess to provide added stiffness and support for the web 86 which extends across the upper end of the recess 40.

As shown in FIGS. 1, 4 and 5, when the pump is in closed or operating position, with the head 17 in its lower position, the camshaft is disposed adjacent the bottom of the cam. Displacement of the handle through an arc of 180° in a counterclockwise direction as viewed in FIG. 1, causes the peripheral surface 38 of the cam to bear on a lower, horizontal bearing surface 41, and the camshaft 30 thus is displaced upwardly, with the camshaft constrained against horizontal movement by the bore in the head 17. When the handle has been pivoted through a 180° arc, the camshaft is disposed at the top of the cam 32, and the pump is in its open position shown in FIGS. 2 and 6. Tubing can then be conveniently loaded and unloaded.

To close the pump, the handle 34 is pivoted in the opposite direction, which causes the cam 32 to bear against upper bearing means 42 on the base, forcing the camshaft 30 and consequently the pump head 17 downward. As the pump approaches its fully closed position, the camshaft 30 reaches the fixed bottom position on the base, and the cam 32 reaches a position of stable equilibrium after the camshaft has pivoted 180°.

According to a feature of the invention, the upper bearing means 42 is adjustable by the use of an adjustment screw assembly 48. The preferred adjustment screw assembly employs a rotatable bearing member 50 at the lower end of the adjustable screw assembly to engage the peripheral surface 38 of the cam in rolling contact during opening and closing of the pump. Rotation of the adjustment screw assembly 48 displaces the bearing member slightly upward or downward to vary the pump occlusion. The adjustment does not affect the 180° rotation of the handle in opening and closing the pump, nor does it change the provision of positions of stable equilibrium approximately 180° apart. The adjustment screw assembly preferably is provided with indicia 52 on its head 54 to provide a visual reference point with respect to indicia 56 on the base 18 and thereby facilitate repetition of desired occlusion adjustments.

The adjustment screw shaft 70 in the illustrated embodiment has external threads on a lower end portion to engage corresponding complementary internal threads on a nut 72 formed integrally with the web 86 which extends across the top of the recess 40. It is desirable that each particular rotational orientation of the screw 48 as indicated by the indicia 52 and 56 correspond to a particular linear position of the screw, which in turn corresponds to a particular degree of occlusion. To this end, rotation of the screw is limited to slightly less than 360° by a dowel pin 74 which is fixed in a transverse bore through an upper, non-threaded portion of the nut 72, extending between a pair of integral rings 76 on the adjustment screw. During assembly of the pump, the adjustment screw shaft 70 is screwed into the nut 72, and the dowel pin 74 is then inserted in the bore and between the rings 76. The shaft 70 is then rotated until the upper ring engages the dowel, preventing further downward travel of the screw shaft. The screw head 54 is then attached to the screw shaft, with the indicia aligned as desired.

The bearing member 50 is installed on the lower end of the screw shaft 70 by drilling an appropriately-dimensioned hole in the tip of the screw, inserting the ball, and subsequently deforming the end of the screw slightly to reduce the diameter of the hole at its lower end so as to ensure retention of the bearing member 50.

To prevent the tubing from being drawn through the pump by the rotation of the rotor, gripping members 58 and 60 are disposed on the head and base of the pump. Each of the gripping members has a pair or rasp plates 62 for engaging the exterior of the tubing. The rasp plates on each of the members 58 on the base are inclined relative to one another at an obtuse angle to define a shallow groove for receiving the tubing. The upper rasp plates 62 on each gripping member 60 are substantially coplanar with each other. The gripping members 58 on the base 18 are preferably spring loaded, whereas the gripping members 60 on the occlusion bed are rigidly backed.

From the foregoing it will be appreciated that the invention provides a novel and improved peristaltic pump. The invention is not limited to the particular embodiment described above or to any particular embodiment. Terms such as "horizontal", "vertical", etc. are used herein only to describe the orientation of the various components relative to one another, when the pump is in an upright position as shown in the drawings. It should be understood that the pump can be operated in various different orientations, and the use of these terms is not intended to imply otherwise, nor to limit the description or claims to a pump disposed in a particular orientation.

The invention is described in the following claims.

What is claimed is:

1. A peristaltic pump comprising:
   a base;
   a rotor supported on said base, said rotor comprising
      a support structure and a plurality of rollers
      mounted thereon;

a pump head defining an occlusion bed and supported on said base so as to be movable between an open position in which said occlusion bed is spaced from said rotor by a relatively large distance to enable loading and unloading of tubing, and a closed position in which said occlusion bed is spaced from said rotor by a relatively small distance to enable effectuation of peristaltic pumping in the tubing; and means for displacing said pump head relative to said base between said open position and said closed position comprising a camshaft having a am fixed thereto, an arm extending outward from said camshaft to facilitate manual rotation thereof, and means on said base and pump head to engage said camshaft and cam such that rotation of said camshaft effects displacement of said pump head between said open position and said closed position;

said means for engaging said cam and camshaft including adjustable bearing means for effecting fine adjustments in the position of the occlusion bed in the closed position so as to vary the occlusion of the tubing;

said adjustable bearing means comprising a screw for engaging said cam, and means for reducing friction between said screw and said cam.

2. A peristaltic pump comprising:

a base;

a rotor supported on said base, said rotor comprising a support structure and a plurality of rollers mounted thereon;

a pump head defining an occlusion bed and supported on said base so as to be movable between an open position in which said occlusion bed is spaced from said rotor by a relatively large distance to enable loading and unloading of tubing, and a closed position in which said occlusion bed is spaced from said rotor by a relatively small distance to enable effectuation of peristaltic pumping in the tubing; and means for displacing said pump head relative to said base between said open position and said closed position comprising a camshaft having a cam fixed thereto, an arm extending outward from said camshaft to facilitate manual rotation thereof, and means on said base and pump head to engage said camshaft and cam such that rotation of said camshaft effects displacement of said pump head between said open position and said closed position;

said means for engaging said cam and camshaft including adjustable bearing means for effecting fine adjustments in the position of the occlusion bed in the closed position so as to vary the occlusion of the tubing;

wherein said adjustable bearing means comprises a screw having a rotatable bearing member disposed on its end for engaging said cam in rolling contact.

3. A peristaltic pump in accordance with claim 2 further comprising indicia for visual reference disposed on said adjustable bearing means and on said occlusion bed to facilitate manual determination of angular displacements of the adjustable bearing means.

4. A peristaltic pump comprising:

a base;

a rotor supported on said base, said rotor comprising a support structure and a plurality of rollers mounted thereon;

a pump head which includes an occlusion bed and which is supported on said base so as to be movable between an open position in which said occlusion bed is spaced from said rotor by a relative large distance to enable loading and unloading of tubing, and a closed position in which said occlusion bed is spaced from said rotor by a relatively small distance to enable effectuation of peristaltic pumping in the tubing; and means for displacing said pump head relative to said base between said open position and said closed position comprising a cam shaft having a cam fixed thereto, an arm extending outward from said cam shaft to facilitate manual rotation thereof, and means on said base and said pump head to engage said cam shaft and cam such that rotation of said cam shaft effects displacement of said pump head between said open position and said closed position;

said cam shaft extending through a bore in said pump head, and through a slot in said base disposed radially relative to said rotor;

said base having a recess formed therein with a bearing surface for limiting radially inward travel of said cam; and adjustable means for engaging said cam comprising an adjustable screw having bearing means on its radial inward end for engaging said cam and limiting radial outward travel of said cam, said screw being mounted on said base;

said bearing means including means to reduce friction between said screw and said cam.

5. A peristaltic pump in accordance with claim 4 wherein said handle is capable of being pivoted through an arc of about 180°, and wherein said cam comprises a substantially circular disk, with a circular cylindrical peripheral surface engaging said bearing surface and bearing means, said cam being mounted eccentrically on said camshaft so that positions of relatively stable equilibrium for said cam are provided about 180° apart.

6. A peristaltic pump in accordance with claim 4 further comprising indicia for visual reference on said adjustment screw and on said base.

7. A peristaltic pump comprising:

a base;

a rotor supported on said base, said rotor comprising a support structure and a plurality of rollers mounted thereon;

a pump head which includes an occlusion bed and which is supported on said base so as to be movable between an open position in which said occlusion bed is spaced from said rotor by a relative large distance to enable loading and unloading of tubing, and a closed position in which said occlusion bed is spaced from said rotor by a relatively small distance to enable effectuation of peristaltic pumping in the tubing; and means for displacing said pump head relative to said base between said open position and said closed position comprising a cam shaft having a cam fixed thereto, an arm extending outward from said cam shaft to facilitate manual rotation thereof, and means on said base and said pump head to engage said cam shaft and cam such that rotation of said cam shaft effects displacement of said pump head between said open position and said closed position;

said cam shaft extending through a bore in said pump head, and through a slot in said base disposed radially relative to said rotor;

said base having a recess formed therein with a bearing surface for limiting radially inward travel of said cam; and adjustable means for engaging said cam comprising an adjustable screw having bearing means on its radial inward end for engaging said cam and limiting radial outward travel of said cam, said screw being mounted on said base;

wherein said bearing means on said adjustment screw comprises a rotatable member which engages said cam in rolling contact.

8. A peristaltic pump comprising:

a base;

a rotor supported on said base, said rotor comprising a support structure and a plurality of rollers mounted thereon;

a pump head which includes an occlusion bed and which is supported on said base so as to be movable between an open position in which said occlusion bed is spaced from said rotor by a relative large distance to enable loading and unloading of tubing, and a closed position in which said occlusion bed is spaced from said rotor by a relatively small distance to enable effectuation of peristaltic pumping in the tubing; and means for displacing said pump head relative to said base between said open position and said closed position comprising a cam shaft having a cam fixed thereto, an arm extending outward from said cam shaft to facilitate manual rotation thereof, and means on said base and said pump head to engage said cam shaft and cam such that rotation of said cam shaft effects displacement of said pump head between said open position and said closed position;

said cam shaft extending through a bore in said pump head, and through a slot in said base disposed radially relative to said rotor;

said base having a recess formed therein with a bearing surface for limiting radially inward travel of said cam; and adjustable means for engaging said cam comprising an adjustable screw having bearing means on its radial inward end for engaging said cam and limiting radial outward travel of said cam, said screw being mounted on said base;

said pump further comprising indicia for visual reference on said adjustment screw and on said base, and means to limit rotation of said adjustment screw to about 360°.

* * * * *

UNITED STATES PATENT AND TRADEMARK OFFICE
CERTIFICATE OF CORRECTION

PATENT NO. : 5,082,429
DATED : January 21, 1992
INVENTOR(S) : Soderquist et al.

It is certified that error appears in the above-identified patent and that said Letters Patent is hereby corrected as shown below:

In column 2, line 5, change "form" to --from--.

In column 2, line 58, after "wall" insert --90--.

In column 5, line 11, Claim 1, change "am" to --cam--.

Signed and Sealed this

Thirteenth Day of April, 1993

Attest:

STEPHEN G. KUNIN

*Attesting Officer*       *Acting Commissioner of Patents and Trademarks*